United States Patent [19]
Dobak, III et al.

[11] Patent Number: 6,096,068
[45] Date of Patent: Aug. 1, 2000

[54] SELECTIVE ORGAN COOLING CATHETER AND METHOD OF USING THE SAME

[75] Inventors: John D. Dobak, III, Del Mar; Juan C. Lasheras, La Jolla, both of Calif.

[73] Assignee: Innercool Therapies, Inc., San Diego, Calif.

[21] Appl. No.: 09/103,342

[22] Filed: Jun. 23, 1998

Related U.S. Application Data

[63] Continuation-in-part of application No. 09/047,012, Mar. 24, 1998, Pat. No. 5,957,963, which is a continuation-in-part of application No. 09/012,287, Jan. 23, 1998.

[51] Int. Cl.[7] .................................................. A61F 7/00
[52] U.S. Cl. ............................................. 607/105; 606/21
[58] Field of Search .................................... 607/104, 105; 606/20–23; 165/DIG. 44, 46, 142, 179, 184; 604/101, 53

[56] References Cited

U.S. PATENT DOCUMENTS

| | | |
|---|---|---|
| 2,308,484 | 1/1943 | Auzin et al. . |
| 2,374,609 | 4/1945 | McCollum . |
| 2,615,686 | 10/1952 | Davidson . |
| 2,672,032 | 3/1954 | Towse ......................................... 62/126 |
| 2,913,009 | 11/1959 | Kuthe . |
| 3,298,371 | 1/1967 | Lee . |
| 3,425,419 | 2/1969 | Dato . |
| 3,504,674 | 4/1970 | Swenson et al. . |
| 3,865,116 | 2/1975 | Brooks . |
| 3,888,259 | 6/1975 | Miley . |
| 3,971,383 | 7/1976 | van Gerven . |
| 4,038,519 | 7/1977 | Foucras . |
| 4,153,048 | 5/1979 | Magrini . |
| 4,190,033 | 2/1980 | Foti . |
| 4,231,425 | 11/1980 | Engstrom . |
| 4,275,734 | 6/1981 | Mitchiner . |
| 4,298,006 | 11/1981 | Parks . |
| 4,318,722 | 3/1982 | Altman . |
| 4,427,009 | 1/1984 | Wells et al. . |
| 4,445,500 | 5/1984 | Osterholm . |
| 4,483,341 | 11/1984 | Witteles . |
| 4,502,286 | 3/1985 | Okada et al. . |
| 4,569,355 | 2/1986 | Bitterly . |

(List continued on next page.)

FOREIGN PATENT DOCUMENTS

| | | |
|---|---|---|
| 0 655 225 A1 | 5/1993 | European Pat. Off. . |
| 0 664 990 | 11/1997 | European Pat. Off. . |
| 2 447 406 | 3/1980 | France . |
| 806 029 | 2/1981 | U.S.S.R. . |
| WO 91/05528 | 5/1991 | WIPO . |
| WO 93/04727 | 3/1993 | WIPO . |
| WO 95/01814 | 1/1995 | WIPO . |
| WO 96/40347 | 12/1996 | WIPO . |
| WO 97/01374 | 1/1997 | WIPO . |
| WO 97/25011 | 7/1997 | WIPO . |
| WO 98/26831 | 6/1998 | WIPO . |
| WO 98/31372 | 7/1998 | WIPO . |

OTHER PUBLICATIONS

Ambrus; The Biphasic Nature and Temperature Dependence of the Activation of Human Plasminogen by Urokinase; May 1979; pp. 339–347; Research Communications in Chemical Pathology and Pharmacology, vol. 24, No. 2.

Bigelow; Hypothermia, Its Possible Role in Cardiac Surgery; Nov. 1950; pp. 849–866; Annals of Surgery, vol. 132, No. 5.

(List continued on next page.)

*Primary Examiner*—Linda C. M. Dvorak
*Assistant Examiner*—Roy Gibson
*Attorney, Agent, or Firm*—Gerald W. Spinks

[57] ABSTRACT

A heat transfer device has first and second elongated, articulated segments, each having a turbulence-inducing exterior surface. A flexible joint connects the first and second elongated, articulated segments. An inner coaxial lumen is disposed within the first and second elongated, articulated segments. The inner coaxial lumen is capable of transporting a pressurized working fluid to a distal end of the first elongated, articulated segment.

38 Claims, 9 Drawing Sheets

U.S. PATENT DOCUMENTS

| | | |
|---|---|---|
| 4,581,017 | 4/1986 | Sahota . |
| 4,655,746 | 4/1987 | Daniels et al. . |
| 4,672,962 | 6/1987 | Hershenson . |
| 4,748,979 | 6/1988 | Hershenson . |
| 4,750,493 | 6/1988 | Brader . |
| 4,762,130 | 8/1988 | Fogarty et al. . |
| 4,860,744 | 8/1989 | Johnson et al. . |
| 4,883,455 | 11/1989 | Leonard . |
| 4,894,164 | 1/1990 | Polaschegg . |
| 4,904,237 | 2/1990 | Janese . |
| 4,920,963 | 5/1990 | Brader . |
| 4,964,409 | 10/1990 | Tremulis . |
| 5,014,695 | 5/1991 | Benak et al. . |
| 5,018,521 | 5/1991 | Campbell . |
| 5,019,075 | 5/1991 | Spears et al. . |
| 5,041,089 | 8/1991 | Mueller et al. . |
| 5,078,713 | 1/1992 | Varney . |
| 5,092,841 | 3/1992 | Spears . |
| 5,106,360 | 4/1992 | Ishwara et al. . |
| 5,108,390 | 4/1992 | Potocky et al. . |
| 5,110,721 | 5/1992 | Anaise et al. . |
| 5,117,822 | 6/1992 | Laghi . |
| 5,147,355 | 9/1992 | Friedman et al. . |
| 5,149,321 | 9/1992 | Klatz et al. . |
| 5,150,706 | 9/1992 | Cox et al. . |
| 5,151,100 | 9/1992 | Abele et al. . |
| 5,190,539 | 3/1993 | Fletcher et al. . |
| 5,191,883 | 3/1993 | Lennox et al. . |
| 5,196,024 | 3/1993 | Barath . |
| 5,211,631 | 5/1993 | Sheaff . |
| 5,234,405 | 8/1993 | Klatz et al. . |
| 5,248,312 | 9/1993 | Langberg . |
| 5,250,070 | 10/1993 | Parodi . |
| 5,257,977 | 11/1993 | Eshel . |
| 5,264,260 | 11/1993 | Saab . |
| 5,269,369 | 12/1993 | Faghri . |
| 5,269,749 | 12/1993 | Koturov . |
| 5,269,758 | 12/1993 | Taheri . |
| 5,281,213 | 1/1994 | Milder et al. . |
| 5,281,215 | 1/1994 | Milder . |
| 5,310,440 | 5/1994 | Zingher . |
| 5,334,193 | 8/1994 | Nardella . |
| 5,342,301 | 8/1994 | Saab . |
| 5,344,436 | 9/1994 | Fontenot et al. . |
| 5,365,750 | 11/1994 | Greenthal . |
| 5,368,591 | 11/1994 | Lennox et al. . |
| 5,383,918 | 1/1995 | Panetta . |
| 5,395,314 | 3/1995 | Klatz et al. . |
| 5,395,331 | 3/1995 | O'Neill et al. . |
| 5,403,281 | 4/1995 | O'Neill et al. . |
| 5,417,686 | 5/1995 | Peterson et al. . |
| 5,423,745 | 6/1995 | Todd et al. ................................ 604/53 |
| 5,423,807 | 6/1995 | Milder . |
| 5,433,740 | 7/1995 | Yamaguchi . |
| 5,437,673 | 8/1995 | Baust et al. . |
| 5,462,521 | 10/1995 | Brucker et al. . |
| 5,486,204 | 1/1996 | Clifton . |
| 5,486,208 | 1/1996 | Ginsburg . |
| 5,531,776 | 7/1996 | Ward et al. . |
| 5,558,644 | 9/1996 | Boyd et al. . |
| 5,573,532 | 11/1996 | Chang et al. ............................ 606/26 |
| 5,584,804 | 12/1996 | Klatz et al. . |
| 5,591,162 | 1/1997 | Fletcher et al. . |
| 5,620,480 | 4/1997 | Rudie . |
| 5,624,392 | 4/1997 | Saab . |
| 5,647,051 | 7/1997 | Neer . |
| 5,713,941 | 2/1998 | Robins et al. . |
| 5,716,386 | 2/1998 | Ward et al. . |
| 5,797,878 | 8/1998 | Bleam . |
| 5,800,480 | 9/1998 | Augustine et al. . |
| 5,807,391 | 9/1998 | Wijkamp ................................... 606/23 |
| 5,824,030 | 10/1998 | Yang et al. . |
| 5,827,222 | 10/1998 | Klatz et al. . |
| 5,827,237 | 10/1998 | Macoviak et al. . |
| 5,833,671 | 11/1998 | Macoviak et al. . |
| 5,837,003 | 11/1998 | Ginsburg . |
| 5,871,526 | 2/1999 | Gibbs et al. . |
| 5,873,835 | 2/1999 | Hastings et al. . |
| 5,879,329 | 3/1999 | Ginsburg . |
| 5,899,899 | 5/1999 | Arless et al. ............................ 606/22 |
| 5,902,268 | 5/1999 | Saab . |
| 5,913,886 | 6/1999 | Soloman . |
| 5,916,242 | 6/1999 | Schwartz . |
| 5,989,238 | 11/1999 | Ginsburg . |

OTHER PUBLICATIONS

Cheatle; Cryostripping the Long and Short Saphenous Veins; Jan. 1993; one page; Br. J. Surg., vol. 80.

Dexter; Blood Warms as It Flows Retrograde from a Femoral Cannulation Site to the Carotic Artery During Cardiopulmonary Bypass; Nov. 1994; pp. 393–397; Perfusion, vol. 9, No. 6.

Gillinov; Superior Cerebral Protection with Profound Hypothermia During Circulatory Arrest; Nov. 1992; pp. 1432–1439; Ann. Thorac. Surg., vol. 55.

Higazi; The Effect of Ultrasonic Irradiation and Temperature on Fibrinolytic Activity in Vitro; Aug. 1992; pp. 251–253; Thrombosis Research, vol. 69, No. 2.

Imamaki; Retrograde Cerebral Perfusion with Hypothermic Blood Provides Efficient Protection of the Brain; Jul. 1995; pp. 325–333; Journal of Cardiac Surgery, vol. 10, No. 4, Part 1.

Jolin; Management of a Giant Intracranial Aneurysm Using Surface–Heparinized Extracorporeal Circulation and Controlled Deep Hypothermic Low Flow Perfusion; Aug. 1992; pp. 756–760; Acta Anaesthesiologica Scandinavia.

Kimoto; Open Heart Surgery under Direct Vision with the Aid of Brain–Cooling by Irrigation; Jul. 1955; pp. 592–603; Surgery, vol. 39, No. 4.

Meden; The Influence of Body Temperature on Infarct vol. and Thrombolytic Therapy in a Rat Embolic Stroke Model; Feb. 1994; pp. 131–138; Brain Research, vol. 647.

Milleret; Abstract of Cryosclerosis of the Saphenous Veins in Varicose Reflux in the Obese and Elderly; Oct. 1981; one page; Phlebologie, vol. 34, No. 4.

Meden; Effect of Hypothermia and Delayed Thrombolysis in a Rat Embolic Stroke Model; Dec. 1993; pp. 91–98; Acta Neurologica Scandinavica.

Parkins; Brain Cooling in the Prevention of Brain Damage during Periods of Circulatory Occlusion in Dogs; Apr. 1954; pp. 284–289; Annals of Surgery, vol. 140, No. 3.

Piepgras; Rapid Active Internal Core Cooling for Induction of Moderate Hypothermia in Head Injury by Use of an Extracorporeal Heat Exchanger; Feb. 1998; pp. 311–318; Neurosurgery, vol. 42, No. 2.

Rijken; Plasminogen Activation at Low Temperatures in Plasma Samples Containing Therapeutic Concentrations of Tissue–Type Plasminogen Activator or Other Thrombolytic Agents; Oct. 1989; pp. 47–52; place of publication unknown.

Schwartz; Cerebral Blood Flow during Low–flow Hypothermic Cardiopulmonary Bypass in Baboons; Jun. 1994; pp. 959–964; Anesthesiology, vol. 81, No. 4.

Schwartz; Selective Cerebral Hypothermia by Means of Transfemoral Internal Carotid Artery Catheterization; May 1996; pp. 571–572; Radiology, vol. 201, No. 2.

Steen; The Detrimental Effects of Prolonged Hypothermia and Rewarming in the Dog; Aug. 1979; pp. 224–230; Anesthesiology, vol. 52, No. 3.

Vandam; Hypothermia; Sep. 1959; pp. 546–553; The New England Journal of Medicine.

White; Cerebral Hypothermia and Circulatory Arrest; Jul. 1978; pp. 450–458; Mayo Clinic Proceedings, vol. 53.

Yenari; Thrombolysis with Tissue Plasminogen Activator (tPA) Is Temperature Dependent; Jul. 1994; pp. 475–481; Thrombosis Research, vol. 77, No. 5.

Yoshihara; Changes in Coagulation and Fibrinolysis Occurring in Dogs during Hypothermia; Aug. 1984; pp. 503–512; Thrombosis Research, vol. 37, No. 4.

Zarins; Circulation in Profound Hypothermia; Nov. 1972; pp. 97–104; Journal of Surgical Research, vol. 14, No. 2.

Jos R.C. Jansen, Ph.D., et al. (1997) Near continuous cardiac output by thermodilution. Journal of Clinical Monitoring 13:233–239.

Cheatle, T.R. et al. (1993) Cryostripping the long and short saphenous veins. Br. J. Surg. 80:1283.

Milleret, Rene La cryo–chirurgie danes les varices des mimbres inferieurs. Angiologie. Supplement au No. 110.

Schwartz, A.E. et al. (1996) Isolated cerebral hypothermia by single carotid artery perfusion of extracorporeally cooled blood in baboons. Neurosurgery 39(3):577–582.

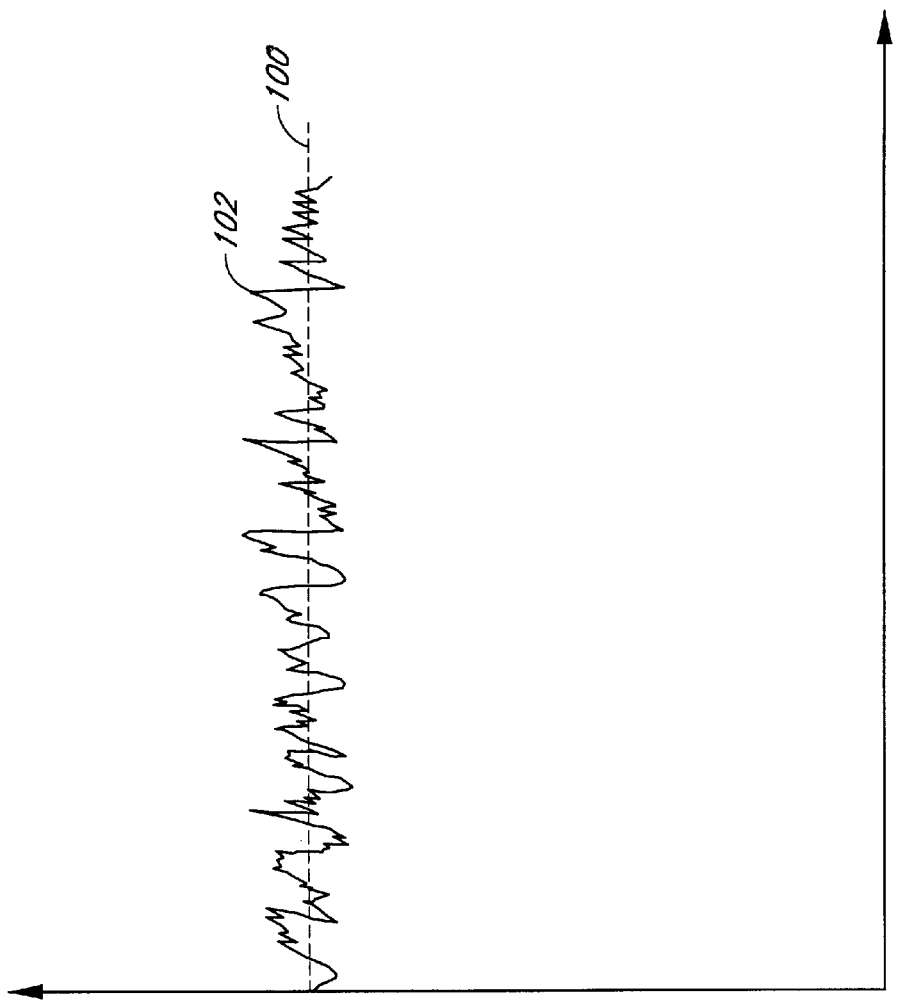

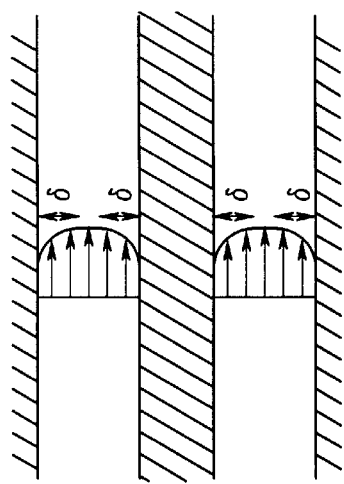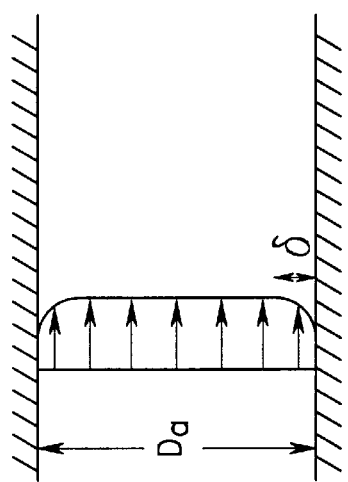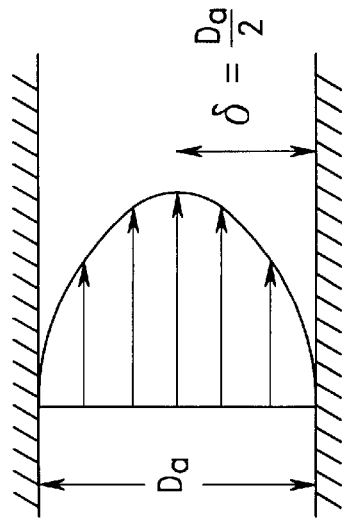

SELECTIVE ORGAN COOLING CATHETER AND METHOD OF USING THE SAME

CROSS REFERENCE TO RELATED APPLICATIONS

This is a continuation-in-part patent application of U.S. patent application Ser. No. 09/047,012, filed on Mar. 24, 1998, now U.S. Pat. No. 5,957,963 and entitled "Improved Selective Organ Hypothermia Method and Apparatus", which is a continuation-in-part patent application of co-pending U.S. patent application Ser. No. 09/012,287, filed on Jan. 23, 1998, and entitled "Selective Organ Hypothermia Method and Apparatus".

BACKGROUND OF THE INVENTION

I. Field of the Invention

The present invention relates generally to the modification and control of the temperature of a selected body organ. More particularly, the invention relates to a method and intravascular apparatus for controlling organ temperature.

II. Description of the Related Art

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. However, the use of total body hypothermia risks certain deleterious systematic vascular effects. For example, total body hypothermia may cause severe derangement of the cardiovascular system, including low cardiac output, elevated systematic resistance, and ventricular fibrillation. Other side effects include renal failure, disseminated intravascular coagulation, and electrolyte disturbances. In addition to the undesirable side effects, total body hypothermia is difficult to administer.

Catheters have been developed which are inserted into the bloodstream of the patient in order to induce total body hypothermia. For example, U.S. Pat. No. 3,425,419 to Dato describes a method and apparatus of lowering and raising the temperature of the human body. The Dato invention is directed towards a method of inducing moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. However, use of the Dato invention implicates the negative effects of total body hypothermia described above.

Due to the problems associated with total body hypothermia, attempts have been made to provide more selective cooling. For example, cooling helmets or head gear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. From a practical standpoint, such devices are cumbersome and may make continued treatment of the patient difficult or impossible.

Selected organ hypothermia has been accomplished using extracorporeal perfusion, as detailed by Arthur E. Schwartz, M. D. et al., in *Isolated Cerebral Hypothermia by Single Carotid Artery Perfusion of Extracorporeally Cooled Blood in Baboons*, which appeared in Vol. 39, No. 3, NEUROSURGERY 577 (September, 1996). In this study, blood was continually withdrawn from baboons through the femoral artery. The blood was cooled by a water bath and then infused through a common carotid artery with its external branches occluded. Using this method, normal heart rhythm, systemic arterial blood pressure and arterial blood gas values were maintained during the hypothermia. This study showed that the brain could be selectively cooled to temperatures of 20° C. without reducing the temperature of the entire body. However, external circulation of blood is not a practical approach for treating humans because the risk of infection, need for anticoagulation, and risk of bleeding is too great. Further, this method requires cannulation of two vessels making it more cumbersome to perform particularly in emergency settings. Even more, percutaneous cannulation of the carotid artery is difficult and potentially fatal due to the associated arterial wall trauma. Finally, this method would be ineffective to cool other organs, such as the kidneys, because the feeding arteries cannot be directly cannulated percutaneously.

Selected organ hypothermia has also been attempted by perfusion of a cold solution such as saline or perflourocarbons. This process is commonly used to protect the heart during heart surgery and is referred to as cardioplegia. Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

Therefore, a practical method and apparatus which modifies and controls the temperature of a selected organ satisfies a long-felt need.

SUMMARY OF THE INVENTION

A heat transfer device comprises first and second elongated, articulated segments, each the segment having a turbulence-inducing exterior surface. A flexible joint can connect the first and second elongated, articulated segments. An inner coaxial lumen may be disposed within the first and second elongated, articulated segments and is capable of transporting a pressurized working fluid to a distal end of the first elongated, articulated segment. In addition, the first and second elongated, articulated segments may have a turbulence-inducing interior surface for inducing turbulence within the pressurized working fluid. The turbulence-inducing exterior surface may be adapted to induce turbulence within a free stream of blood flow when placed within an artery. The turbulence-inducing exterior surface may be adapted to induce a turbulence intensity with in a free stream blood flow which is greater than 0.05. In one embodiment, the flexible joint comprises bellows sections which allow for the axial compression of the heat transfer device.

In one embodiment, the turbulence-inducing exterior surfaces comprise invaginations configured to have a depth which is greater than a thickness of a boundary layer of blood which develops within an arterial blood flow. The first elongated, articulated segment may comprise counter-clockwise invaginations while the second elongated, articulated segment comprises clockwise invaginations. The first and second elongated, articulated segments may be formed from highly conductive material.

In another embodiment, the turbulence-inducing exterior surface is adapted to induce turbulence throughout the duration of each pulse of a pulsatile blood flow when placed within an artery. In still another embodiment, the turbulence-inducing exterior surface is adapted to induce turbulence during at least 20% of the period of each cardiac cycle when placed within an artery.

The heat transfer device may also have a coaxial supply catheter with an inner catheter lumen coupled to the inner coaxial lumen within the first and second elongated, articulated segments. A working fluid supply configured to dispense the pressurized working fluid may be coupled to the inner catheter lumen. The working fluid supply may be configured to produce the pressurized working fluid at a temperature of about 0° C. and at a pressure below 5 atmospheres of pressure.

In yet another alternative embodiment, the heat transfer device may also have a third elongated, articulated segment having a turbulence-inducing exterior surface and a second flexible joint connecting the second and third elongated, articulated segments. In one embodiment, the first and third elongated, articulated segments may comprise clockwise invaginations if the second elongated, articulated segment comprises counter-clockwise invaginations. Alternatively, the first and third elongated, articulated segments may comprise counter-clockwise invaginations if the second elongated, articulated segment comprises clockwise invaginations.

The turbulence-inducing exterior surface may optionally include a surface coating or treatment to inhibit clot formation. One variation of the heat transfer device comprises a stent coupled to a distal end of the first elongated, articulated segment.

The present invention also envisions a method of treating the brain which comprises the steps of inserting a flexible, conductive heat transfer element into the carotid artery from a distal location, and circulating a working fluid through the flexible, conductive heat transfer element in order to selectively modify the temperature of the brain without significantly modifying the temperature of the entire body. The flexible, conductive heat transfer element preferably absorbs more than 25, 50 or 75 Watts of heat.

The method may also comprise the step of inducing turbulence within the free stream blood flow within the carotid artery. In one embodiment, the method includes the step of inducing blood turbulence with a turbulence intensity greater than 0.05 within the carotid artery. In another embodiment, the method includes the step of inducing blood turbulence throughout the duration of the period of the cardiac cycle within the carotid artery. In yet another embodiment, the method comprises the step of inducing blood turbulence throughout the period of the cardiac cycle-within the carotid artery or during greater than 20% of the period of the cardiac cycle within the carotid artery. The step of circulating may comprise the step of inducing turbulent flow of the working fluid through the flexible, conductive heat transfer element. The pressure of the working fluid may be maintained below 5 atmospheres of pressure.

The present invention also envisions a method for selectively cooling an organ in the body of a patient which comprises the steps of introducing a catheter into a blood vessel supplying the organ, the catheter having a diameter of 4 mm or less, inducing free stream turbulence in blood flowing over the catheter, and cooling the catheter to remove heat from the blood to cool the organ without substantially cooling the entire body. In one embodiment, the cooling step removes at least about 75 Watts of heat from the blood. In another embodiment, the cooling step removes at least about 100 Watts of heat from the blood. The organ being cooled may be the human brain.

The step of inducing free stream turbulence may induce a turbulence intensity greater than 0.05 within the blood vessel. The step of inducing free stream turbulence may induce turbulence throughout the duration of each pulse of blood flow. The step of inducing free stream turbulence may induce turbulence for at least 20% of the duration of each pulse of blood flow.

In one embodiment, the catheter has a flexible metal tip and the cooling step occurs at the tip. The tip may have turbulence-inducing segments separated by bellows sections. The turbulence-inducing segments may comprise invaginations which are configured to have a depth which is greater than a thickness of a boundary layer of blood which develops within the blood vessel. In another embodiment, the catheter has a tip at which the cooling step occurs and the tip has turbulence inducing sections that alternately spiral bias blood flow in clockwise and counterclockwise directions.

The cooing step may comprise the step of circulating a working fluid in through an inner lumen in the catheter and out through an outer, coaxial lumen. In one embodiment, the working fluid remains a liquid. The working fluid may be aqueous.

The present invention also envisions a cooling catheter comprising a catheter shaft having first and second lumens therein. The cooling catheter also comprises a cooling tip adapted to transfer heat to or from a working fluid circulated in through the first lumen and out through the second lumen, and turbulence-inducing structures on the cooling tip capable of inducing free stream turbulence when the tip is inserted into a blood vessel. The turbulence-inducing structures may induce a turbulence intensity of at least about 0.05. The cooling tip may be adapted to induce turbulence within the working fluid. The catheter is capable of removing least about 25 Watts of heat from an organ when inserted into a vessel supplying that organ, while cooling the tip with a working fluid that remains a liquid in the catheter. Alternatively, the catheter is capable of removing at least about 50 or 75 Watts of heat from an organ when inserted into a vessel supplying that organ, while cooling the tip with an aqueous working fluid. In one embodiment, in use, the tip has a diameter of 4 mm or less. Optionally, the turbulence-inducing structures comprise invaginations which have a depth sufficient to disrupt the free stream blood flow in the blood vessel. Alternatively, the turbulence-inducing structures may comprise staggered protrusions which have a height sufficient to disrupt the free stream flow of blood within the blood vessel.

In another embodiment, a cooling catheter may comprise a catheter shaft having first and second lumens therein, a cooling tip adapted to transfer heat to or from a working fluid circulated in through the first lumen and out through the second lumen, and turbulence-inducing structures on the cooling tip capable of inducing turbulence when the tip is inserted into a blood vessel. Alternatively, a cooling catheter may comprise a catheter shaft having first and second lumens therein, a cooling tip adapted to transfer heat to or from a working fluid circulated in through the first lumen and out through the second lumen, and structures on the cooling tip capable of inducing free stream turbulence when the tip is inserted into a blood vessel. In another embodiment, a cooling catheter may comprise a catheter shaft having first and second lumens therein, a cooling tip adapted to transfer heat to or from a working fluid circulated in through the first lumen and out through the second lumen, and turbulence-inducing structures on the cooling tip capable of inducing turbulence with an intensity greater than about 0.05 when the tip is inserted into a blood vessel.

BRIEF DESCRIPTION OF THE DRAWINGS

The features, objects, and advantages of the invention will become more apparent from the detailed description set forth below when taken in conjunction with the drawings in which like reference characters identify corresponding throughout and wherein:

FIG. 1 is a graph illustrating the velocity of steady state turbulent flow as a function of time.

FIG. 3A is a velocity profile diagram showing a typical steady state Poiseuillean flow driven by constant pressure gradient.

FIG. 3B is a velocity profile diagram showing blood flow velocity within an artery averaged over the cardiac pulse.

FIG. 3C is a velocity profile diagram showing blood flow velocity within an artery averaged over the cardiac pulse upon insertion of a smooth heat transfer element within a blood vessel.

DETAILED DESCRIPTION OF THE INVENTION

Figure 2A:
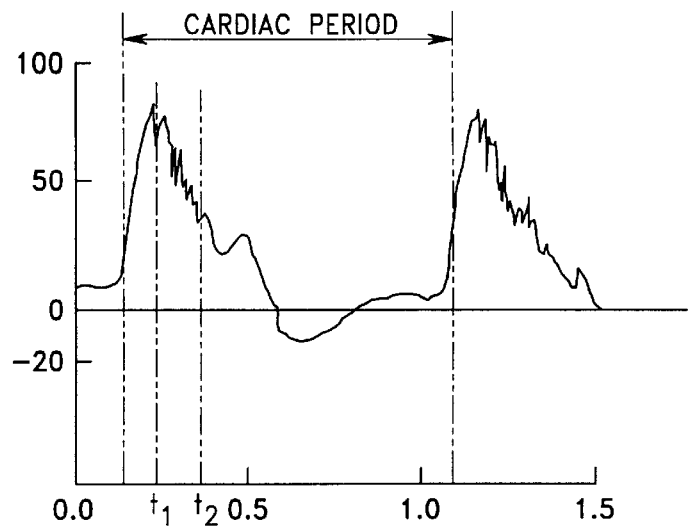
FIG. 2A is a graph showing the velocity of the blood flow within an artery as a function of time.

In order to intravascularly regulate the temperature of a selected organ, a heat transfer element may be placed in the feeding artery of the organ to absorb or deliver the heat from or to the blood flowing into the organ. The transfer of heat may cause either a cooling or a heating of the selected organ. The heat transfer element must be small enough to fit within the feeding artery while still allowing a sufficient blood flow to reach the organ in order to avoid ischemic organ damage. A heat transfer element which selectively cools an organ should be capable of providing the necessary heat transfer rate to produce the desired cooling or heating effect within the organ. By placing the heat transfer element within the feeding artery of an organ, the temperature of an organ can be controlled without significantly effecting the remaining parts of the body. These points can be illustrated by using brain cooling as an example.

The common carotid artery supplies blood to the head and brain. The internal carotid artery branches off of the common carotid to directly supply blood to the brain. To selectively cool the brain, the heat transfer element is placed into the common carotid artery, the internal carotid artery, or both. The internal diameter of the common carotid artery ranges from 6 to 8 mm and the length ranges from 80 to 120 mm. Thus, the heat transfer element residing in one of these arteries cannot be much larger than 4 mm in diameter in order to avoid occluding the vessel.

It is important that the heat transfer element be flexible in order to be placed within the small feeding artery of an organ. Feeding arteries, like the carotid artery, branch off the aorta at various levels. Subsidiary arteries continue to branch off the initial branches. For example, the internal carotid artery is a small diameter artery that branches off of a common carotid artery near the angle of the jaw. Because the heat transfer element is typically inserted into a peripheral artery, such as the femoral artery, and accesses the feeding artery by initially passing though a series of one or more of these branch, the flexibility of the heat transfer element is an important characteristic of the heat transfer element. Further, the heat transfer element is ideally constructed from a high thermally conductive material such as metal in order to facilitate heat transfer. The use of a high thermally conductive material increases the heat transfer rate for a given temperature differential between the coolant within the heat transfer element and the blood. This facilitates the use of a higher temperature coolant within the heat transfer element, allowing safer coolants such as water to be used. High thermally conductive materials, such as metals, tend to be rigid. The design of the heat transfer element should facilitate flexibility in an inherently inflexible material.

In order to obtain the benefits of hypothermia described above, it is desirable to reduce the temperature of the blood flowing to the brain to between 30° C. and 32° C. Given that a typical brain has a blood flow rate through each carotid artery (right and left) of approximately 250–375 cubic centimeters per minute (cc/min), the heat transfer element should absorb 75–175 Watts of heat when placed in one of the carotid arteries in order to induce the desired cooling effect. It should be noted that smaller organs may have less blood flow in the supply artery and may require less heat transfer such as 25 Watts.

When a heat transfer element is inserted coaxially into an artery, the primary mechanism of heat transfer between the surface of the heat transfer element and the blood is forced convection. Convection relies upon the movement of fluid to transfer heat. Forced convection results when an external force causes motion within the fluid. In the case of arterial flow, the beating heart causes the motion of the blood around the heat transfer element.

Equation 1 is Newton's law of convection which provides an estimate of the rate of heat transfer between the blood and the heat transfer element.

$$Q = \overline{h}_c S \Delta T \qquad \text{Equation 1}$$

where Q is the heat transfer rate in Watts;
S is the area of the heat transfer element in direct contact with the fluid in meters squared ($m^2$);
$\Delta T$ is the temperature differential between the surface temperature, $T_s$, of the heat transfer element and the free stream blood temperature, $T_b$, in degrees Kelvin (K); and
$\overline{h}_c$ is the average convection heat transfer coefficient over the heat transfer area in units of Watts per meter squared degrees Kelvin (W/$m^2$K), and is some times called the surface coefficient of heat transfer or the convection heat transfer coefficient.

The magnitude of the heat transfer rate, Q, can be increased through manipulation of the three parameters which determine its value: $\overline{h}_c$, S, and $\Delta T$. Practical constraints limit the value of these parameters.

As noted above, the receiving artery into which the heat transfer element is placed has a limited diameter and length. Thus, the cross sectional area of the heat transfer element should be limited so as to avoid significant obstruction of the blood flow through the artery. The length of the heat transfer element should also be limited so that the heat transfer element is small enough to fit into the receiving artery. For placement within the internal and common carotid artery, the cross sectional diameter of the heat transfer element is limited to about 4 mm, and its length is limited to approximately 10 cm. Consequently, the value of the surface area, S, is limited by the physical constraints imposed by the size of the artery into which the device is placed. Surface features, such as fins, can be used to increase the surface area of the heat transfer element, however, these features alone cannot provide enough surface area enhancement to meet the required heat transfer rate to effectively cool the brain.

For the case where the heat transfer element is used to induce hypothermia, the value of $\Delta T = T_b - T_s$ can be increased by decreasing the surface temperature, $T_s$, of the heat transfer element. However, the allowable surface temperature is limited by the characteristics of blood. Blood freezes at approximately 0° C. When the blood approaches freezing, ice emboli may form in the blood which may lodge downstream, causing serious ischemic injury. Furthermore, reducing the temperature of the blood also increases its viscosity which also results in a small decrease in the value of the convection heat transfer coefficient, $\overline{h}_c$. In addition, increased viscosity of the blood may result in an increase in the pressure drop within the artery, thus, compromising the flow of blood to the brain. Given the above constraints, it is advantageous to limit the surface temperature of the heat transfer element to approximately 5° C., thus, resulting in a maximum temperature differential between the blood stream and the heat transfer element of approximately 32° C.

The mechanisms by which the value of convection heat transfer coefficient, $\overline{h}_c$, may be increased are complex. However, it is well known that the convection heat transfer coefficient, $\overline{h}_c$, increases with the level of turbulent kinetic energy in the fluid flow. Thus it is advantageous to have turbulent blood flow in contact with the heat transfer element.

Arterial blood flow is completely bound by a solid surface (i.e. the arterial wall) and is called an internal flow. Internal flows may be characterized as laminar or turbulent. In the laminar regime, flow structure is characterized by smooth motion in laminae or layers. Laminar flow has no turbulent kinetic energy. Flow structure in the turbulent regime is characterized by random, three-dimensional motions of fluid particles superimposed on the mean motion. FIG. 1 is a graph illustrating steady state turbulent flow. The vertical axis is the velocity of the flow. The horizontal axis represents time. The average velocity of the turbulent flow is shown by a line 100. The actual instantaneous velocity of the flow is shown by a curve 102.

The level of turbulence can be characterized by the turbulence intensity. Turbulence intensity, $\vartheta$, is defined as the square root of the fluctuating velocity divided by the mean velocity as given in Equation 2.

$$\vartheta = \frac{\sqrt{(u')^2}}{\overline{u}} \qquad \text{Equation 2}$$

where u' is the magnitude of the time-varying portion of the velocity; and
$\overline{u}$ is the average velocity.

For example, referring again to FIG. 1, the velocity of the time-varying portion of the velocity, u', is represented by the size of the peaks and valleys on the curve 102. The average velocity, $\overline{u}$, is represented by the line 100.

The most basic fluid mechanic equations predict the behavior of internal pipe flows under a uniform and constant pressure. Under these conditions the flow is Poiseuillean. FIG. 3A is a velocity profile diagram showing a typical steady state Poiseuillean flow driven by constant pressure. The velocity of the fluid across the pipe is shown in FIG. 3A by the parabolic curve and corresponding velocity vectors. The velocity of the fluid in contact with the wall of the pipe is zero. The boundary layer is the region of the flow in contact with the pipe surface in which viscous stresses are dominant. In the steady state Poiseuillean flow, the boundary layer develops until it reaches the pipe center line. For example, the boundary layer thickness, $\delta$, in FIG. 3A is one half of the diameter of the pipe, $D_a$. FIG. 3A is introduced for comparison purposes to show the difference between standard Poiseuillean flow and the flow which develops within an artery.

Under conditions of Poiseuillean flow, the Reynolds number, Re, can be used to characterize the level of turbulent kinetic energy. The Reynolds number, Re, is the ratio of inertial forces to viscous forces and is given by Equation 3:

$$Re = \frac{U D_a \rho}{\mu} \qquad \text{Equation 3}$$

where: $D_a$ is the diameter of the artery in meters (m);
U is the flow velocity of the blood in meters/second (m/s);

ρ is the density of the blood in kilograms per meters cubed (kg/m³); and

μ is the absolute viscosity of the blood in meters squared per second (m³/s).

For Poiseuillean flows, Reynolds numbers, Re, must be greater than about 2300 to cause a laminar to turbulent transition. Further, under conditions of high Reynolds numbers (>2000), the boundary layer is receptive to "tripping". Tripping is a process by which a small perturbation in the boundary layer amplifies to turbulent conditions. The receptivity of a boundary layer to "tripping" is proportional to the Reynolds, Re, number and is nearly zero for Reynolds, Re, numbers less than 2000.

However, the blood flow in the arteries is induced by the beating heart and is pulsatile, complicating the turbulent fluid mechanics analysis above. FIG. 2A is a graph showing the velocity of the blood flow within an artery as a function of time. The beating heart provides pulsatile flow with an approximate period of 0.5 to 1 second. This is known as the period of the cardiac cycle. The horizontal axis in FIG. 2A represents time in seconds and the vertical axis represents the average velocity of blood in centimeters per second (cm/s). Although very high velocities are reached at the peak of the pulse, the high velocity occurs for only a small portion of the cycle. In fact, the velocity of the blood reaches zero in the carotid artery at the end of a pulse and temporarily reverses.

Because of the relatively short duration of the cardiac pulse, the blood flow in the arteries does not develop into classic Poiseuillean flow. FIG. 3B is a velocity profile diagram showing blood flow velocity within an artery averaged over the cardiac pulse. Notice that the majority of the flow within the artery has the same velocity. The character of the pulsed flow in an artery of diameter, $D_a$, is determined by the value of a dimensionless parameter called the Womersley number. The Womersley number expresses the ratio between oscillatory inertia forces and viscous shear forces and is also proportional to the interior diameter of the artery and inversely proportional to the thickness of the boundary layer as given in Equation 4.

$$N_w = \sqrt{\frac{\rho D_a^2 \omega}{\mu}} \propto \frac{D_a}{\delta} \qquad \text{Equation 4}$$

where ω is the frequency of the pulsating force in cycles per second (1/s);

$D_a$ is the diameter of the artery in meters (m);

ρ is the density of the blood in kilograms per meters cubed (kg/m³);

μ is the absolute viscosity of the blood in meters squared per second (m³/s); and δ is the boundary layer thickness in meters (m).

The Womersley number is relatively high ($N_w$=15–20) in the aorta and in the common carotid artery ($N_w$=6–10). The relatively high Womersley numbers results in the relatively blunt velocity profile in contrast to the parabolic profile of the steady state viscous Poiseuillean flow. In other words, the arterial flow is predominately composed of an inviscid "free stream" and a very thin viscous boundary layer adjacent to the artery wall. "Free stream" refers to the flow which is not affected by the presence of the solid boundaries and in which the average velocity remains fairly constant as a function of position within the artery. The motion in the boundary layer is mainly the result of the balance between inertia and viscous forces, while in the free stream, the motion is the result of the balance between inertia and pressure forces. In FIG. 3B, notice that the boundary layer where the flow velocity decays from the free stream value to zero is very thin, typically ⅙ to ½₀ of the diameter of the artery, as opposed to one half of the diameter of the artery in the Poiseuillean flow condition.

As noted above, if the flow in the artery were steady rather than pulsatile, the transition from laminar to turbulent flow would occur when the value of the Reynolds number, Re, exceeds about 2,300. However, in the pulsatile arterial flow, the value of the Reynolds number, Re, varies during the cardiac cycle, just as the flow velocity, U, varies. In pulsatile flows, due to the enhanced stability of associated with the acceleration of the free stream flow, the critical value of the Reynolds number, Re, at which the unstable modes of motion grow into turbulence is found to be much higher, perhaps as high as 9,000. The critical value of the Reynolds number, Re, at which laminar flow transitions into turbulent flow increases with increasing values of the Womersley number. Consequently, the blood flow in the arteries of interest remains laminar over more than 80% of the cardiac cycle. Referring again to FIG. 2A, the blood flow is turbulent from approximately time $t_1$ until time $t_2$ during a small portion of the descending systolic flow which is less than 20% of the period of the cardiac cycle. It can be seen from FIG. 2A that turbulence does occur for a short period in the cardiac cycle. If a heat transfer element is placed co axially inside the artery, the heat transfer rate will be facilitated during this short interval. However, to transfer the necessary heat to cool the brain, turbulent kinetic energy may be produced and may be sustained throughout the entire period of the cardiac cycle. The existence of a free stream becomes significant when designing a heat transfer element to transfer heat from a selected organ. Because of the acceleration of the free stream and its inherent stability, simple surface features on the heat transfer element, such as fins or wires, will not produce a laminar to turbulent transition.

A thin boundary layer is noted to form during thecardiac cycle. This boundary layer will form over the surface of a smooth heat transfer element. FIG. 3C is a velocity profile diagram showing blood flow velocity within an artery averaged over the cardiac pulse upon insertion of a smooth heat transfer element 18 within a blood vessel. In FIG. 3C, the diameter of the heat transfer element 18, D, is about one half of the diameter of the artery, $D_a$. Notice that boundary layers develop adjacent to the heat transfer element 18 as well as the walls of the artery. Each of these boundary layers has approximately the same thickness, δ, as the boundary layer which would have developed at the wall of the artery in the absence of the heat transfer element 18. The free stream flow region is developed in an annular ring around the heat transfer element 18.

One way to increase the heat transfer rate is to create a turbulent boundary layer on the heat transfer element surface. However, "tripping" mechanisms, such as placing a wire or fin on the smooth surface of the heat transfer element shown, will not work. This is due to the low Reynolds numbers in arterial flow which are less than 250 for more than half the cycle (i.e. the receptivity to tripping is extremely low).

The arterial flow is predominantly free stream and inherently stable such that very high Reynolds number must be found before a laminar to turbulent transition takes place. Although a thin boundary layer forms, simple fins or coiled wires on a heat transfer element will not produce sustained turbulent kinetic energy in the boundary layer and produce the necessary heat transfer rate. Therefore, to induce turbulent kinetic energy and increase the heat transfer rate sufficiently to cool the brain by a catheter placed in the common carotid, stirring type mechanisms, which abruptly change the direction of velocity vectors, may be utilized. This can create high levels of turbulence intensity in the free stream thereby increasing the heat transfer rate.

Figure 2B:
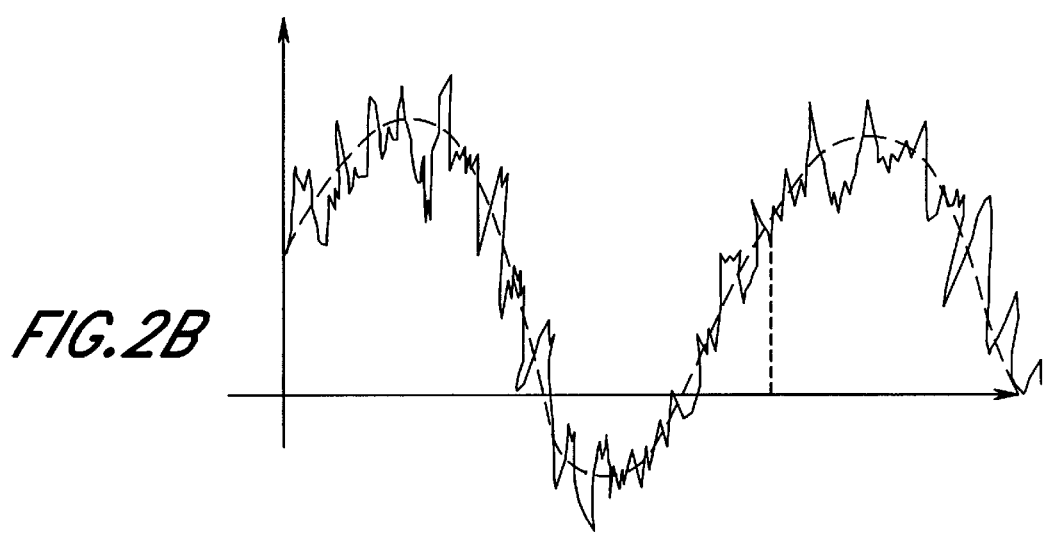
FIG. 2B is a graph of illustrating the velocity of steady state turbulent flow under pulsatile conditions as a function of time similar to those seen in arterial blood flow.
Figure 2C:
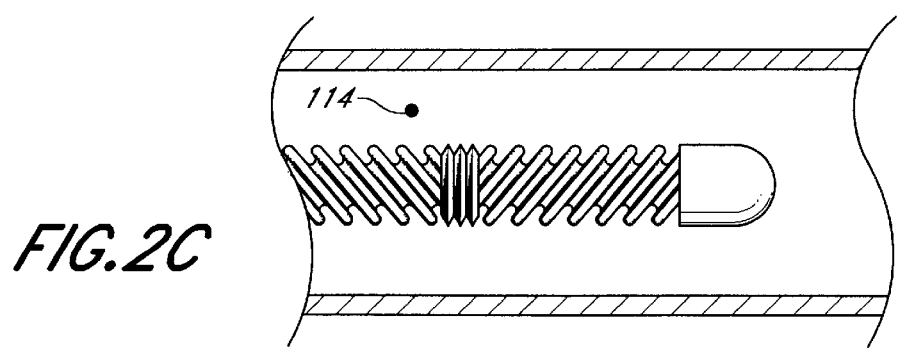
FIG. 2C is a perspective view of a turbulence inducing heat transfer element within an artery which indicates where the turbulent flow is measured within the artery in relation to the heat transfer element.

This turbulence intensity should ideally be sustained for a significant portion of the cardiac cycle. The turbulent kinetic energy should ideally be created throughout the free stream and not just in the boundary layer. FIG. 2B is a graph illustrating the velocity of steady state turbulent flow under pulsatile conditions as a function of time similar to those seen in an arterial blood flow. FIG. 2C is a perspective view of a turbulence inducing heat transfer element within an artery which indicates point 114 where the turbulent flow is measured within the artery in relationship to the heat transfer element. Note that turbulent velocity fluctuations are seen throughout the cycle as opposed to the short interval of fluctuations seen in FIG. 2A between time $t_1$ until time $t_2$. These velocity fluctuations are found within the free stream. The turbulence intensity is at least 0.05. In other words, the instantaneous velocity fluctuations deviate from the mean velocity by at least 5%. Although ideally turbulence is created throughout the entire period of the cardiac cycle, the benefits of turbulence are obtained if the turbulence is sustained for 75%, 50% or even as low as 30% or 20% of the cardiac cycle.

To create the desired level of turbulence intensity in the blood free stream during the whole cardiac cycle, in one embodiment, the invention uses a modular design which produces high level of turbulence in the free stream by periodically forcing abrupt changes in the direction of the blood flow. The abrupt changes in flow direction are achieved through the use of a series of two or more segments each comprised of invaginations or protrusions. To affect the free stream, the size of the invaginations or protrusions is larger than the thickness of the boundary layer which would develop if a smooth heat transfer element would be introduced into the blood stream.

The use of periodic abrupt changes in the direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry.

Figure 4:
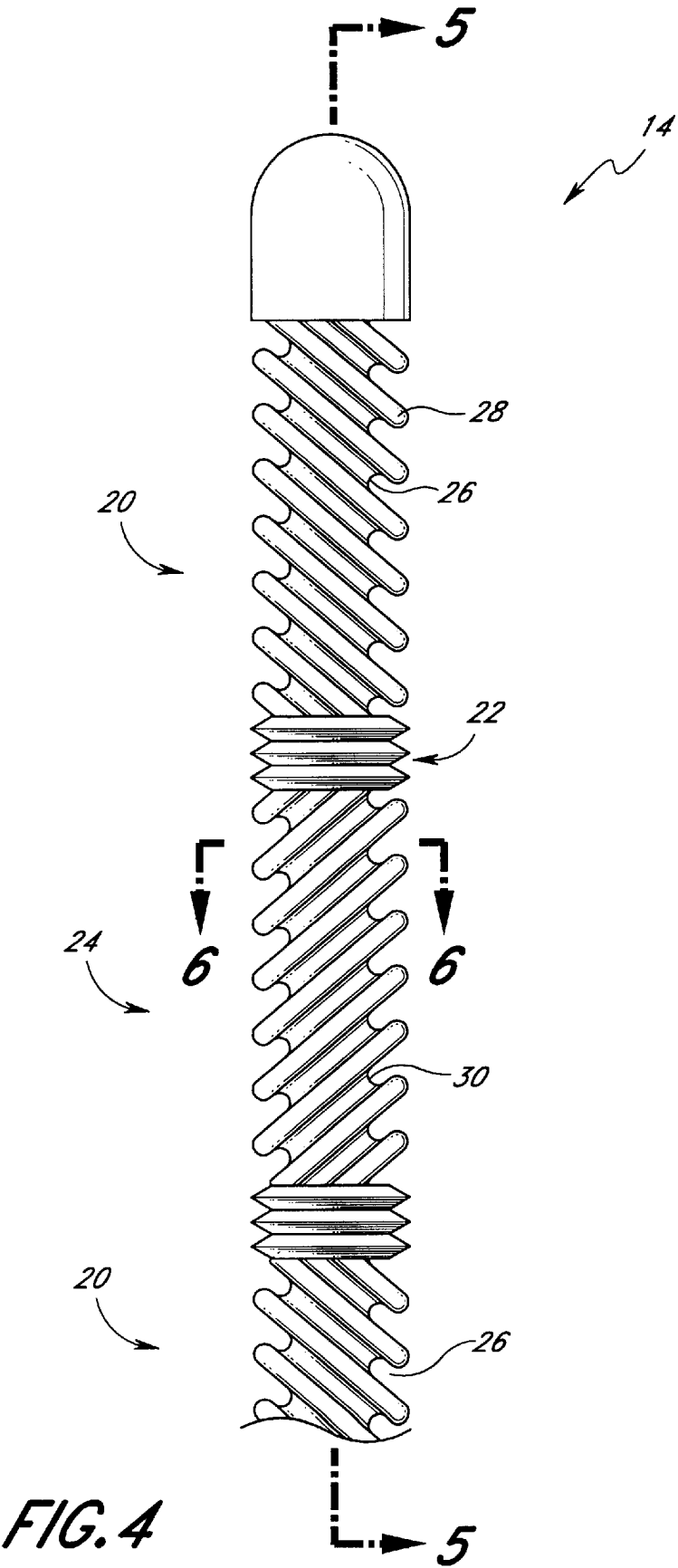
FIG. 4 is a perspective view of one embodiment of a heat transfer element according to the invention.

FIG. 4 is a perspective view of one embodiment of a heat transfer element according to the present invention. A heat transfer element 14 is comprised of a series of articulating segments or modules. As seen in FIG. 4, a first articulating segment 20 is located at the distal end of the heat transfer element 14. A turbulence-inducing exterior surface 28 of the segment 20 is formed from one or more invaginations 26. Within the segment 20, the spiraling invaginations 26 rotate in a clockwise direction as they proceed towards the distal end of the heat transfer element 14. The segment 20 is coupled to a second segment 24 via a bellows section 22 to provide flexibility. The second segment 24 is formed from one or more spiraling invaginations 30. The spiraling invaginations 30 rotate in a counter-clockwise direction as they proceed towards the distal end of the heat transfer element 14. The segment 24 is followed by a third segment 20 having the clockwise invaginations 26. Thus, successive segments of the heat transfer element 14 alternate between having clockwise and counterclockwise invaginations. In addition, the rounded invaginations also allow the heat transfer element to maintain a relatively atraumatic profile in comparison to the use of ribs or fins, thereby minimizing the possibility of damage to the vessel wall. A heat transfer element may be comprised of 1, 2, 3 or more segments.

The bellows sections 22 are formed from seamless and nonporous materials, such as metal, and therefore are impermeable to gas which can be particularly important depending on the type of working fluid which is cycled through the heat transfer element 14. The structure of the bellows sections 22 allows them to bend, extend and compress which increases the flexibility of the heat transfer element so that it is more readily able to navigate through tiny blood vessels. The bellows sections 22 also provide for axial compression of the heat transfer element 14 which can limit the trauma when the distal end of the heat transfer element 14 abuts a blood vessel wall. The bellows sections 22 are also able to tolerate cryogenic temperatures without a loss of performance.

The exterior surface 28 of the heat transfer element 14 can be made from metal, and may comprise very high thermally conductive material such as nickel, thereby, facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities which is an important feature in a disposable medical device.

Because the heat transfer element 14 may dwell within the blood vessel for extended periods of time such as 24–48 hours or even longer, it may be desirable to treat the surface 28 of the heat transfer element 14 to avoid clot formation. In particular, one may wish to treat the bellows sections 22 because stagnation of the blood flow may occur in the convolutions, thus, allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surface 28 of the heat transfer element 14 may be bombarded with ions such as nitrogen. Bombardment with nitrogen can harden and smooth the surface 28 and, thus, prevent adherence of clotting factors to the surface 28.

Figure 5:
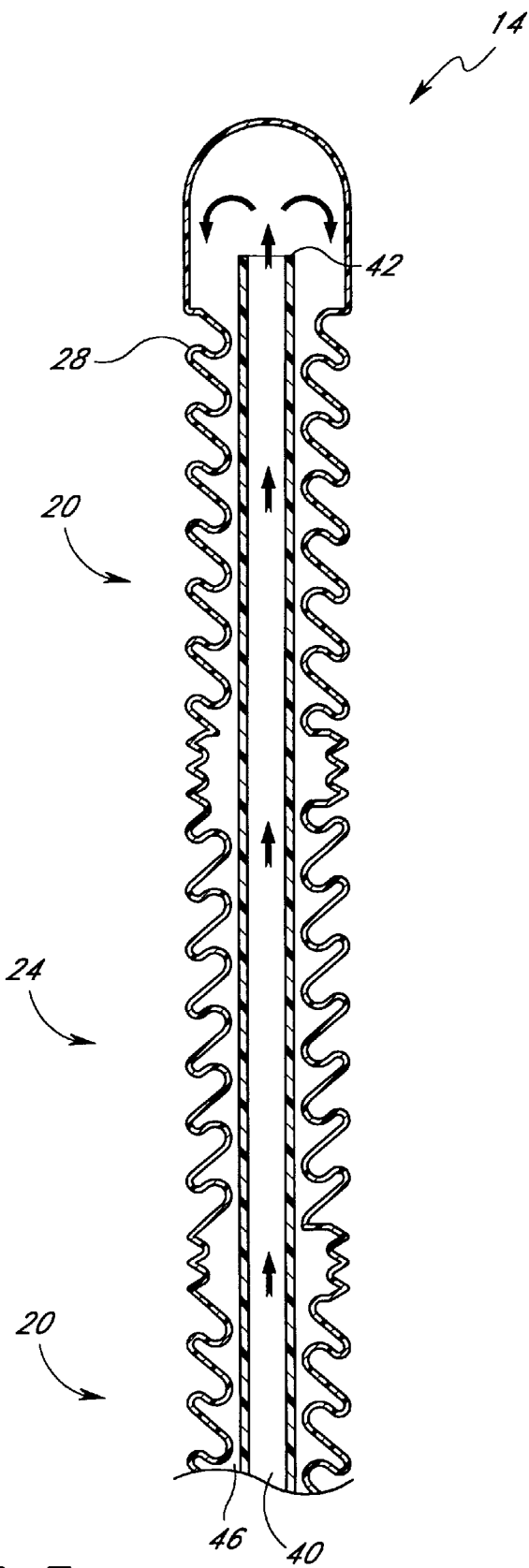
FIG. 5 is longitudinal sectional view of the heat transfer element of FIG. 4.

FIG. 5 is longitudinal sectional view of the heat transfer element of the invention, taken along line 5—5 in FIG. 4. Once the heat transfer element 14 is in place, a working fluid such as saline or other aqueous solution may be circulated through the heat transfer element 14. Fluid flows up a supply catheter into an insulated inner coaxial lumen 40. At the distal end of the heat transfer element 14, the working fluid exits the inner coaxial lumen 40 and enters an outer lumen 46. As the working fluid flows through the outer lumen 46, heat is transferred from the working fluid to the exterior surface 28 of the heat transfer element 14. Because the heat transfer element 14 is constructed from highly conductive material, the temperature of the external surface 28 may reach very close to the temperature of the working fluid. In order to avoid the loss of thermal energy from the working fluid within the inner coaxial lumen 40, an insulating coaxial layer 42 may be provided within the heat transfer element 14. The insulating coaxial layer 42 is comprised of a non-thermally conductive material. For example, insulation may be achieved by creating longitudinal air channels in the walls of the insulating coaxial layer 42. Alternatively, the insulating coaxial layer 42 may be constructed of a non-thermally conductive material like polytetrafluoroethylene or other polymer.

It is important to note that the same mechanisms that govern the heat transfer rate between the external surface 28 of the heat transfer element and the blood also govern the heat transfer rate between the working fluid and the inside surface of the heat transfer element. The heat transfer characteristics of the internal structure is particularly important when using water, saline or other fluid which remains a liquid as the coolant. Other coolants such as freon, undergo nucleated boiling and create turbulence through a different mechanism. Saline is a safe coolant because it is non toxic and leakage of saline does not result in a gas embolism which may occur with the use of boiling refrigerants. By also enhancing turbulence in the coolant, the coolant can be delivered to the heat transfer element at a warmer temperature and still achieve the necessary heat transfer rate. This has a number of beneficial implications in the need for insulation along the catheter shaft length. Due to the decreased need for insulation, the catheter shaft diameter can be made smaller. The enhanced heat transfer characteristics of the internal structure also allow the working fluid to be delivered to the heat transfer element at lower flow rates and lower pressures. High pressures may make the heat transfer element stiff and cause it to push against the wall of the vessel, thereby shielding part of the heat transfer unit from the blood. Because of the increased heat transfer characteristics, the pressure of the working fluid may be as low as 5 atmospheres, 3 atmospheres, 2 atmospheres or even less than 1 atmosphere.

Figure 6:
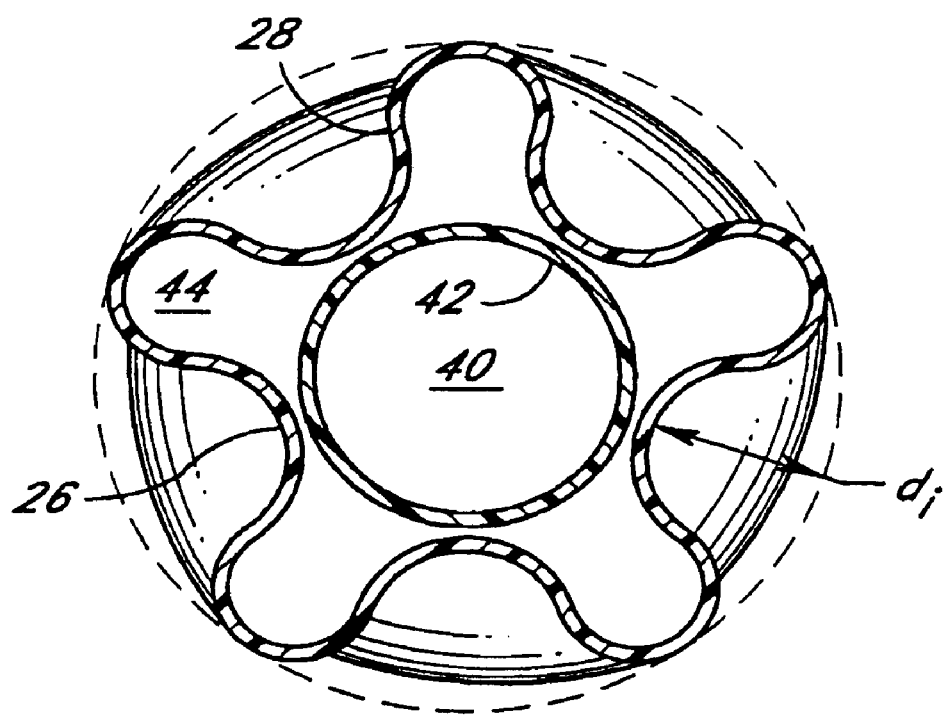
FIG. 6 is a transverse cross-sectional conceptual view of the heat transfer element of FIG. 4.

FIG. 6 is a transverse cross-sectional conceptual view of the heat transfer element of the invention, taken along the line 6—6 in FIG. 4. In FIG. 6, the coaxial construction of the heat transfer element 14 is clearly shown. The inner coaxial lumen 40 is defined by the insulating coaxial layer 42. The outer lumen 44 is defined by the exterior surface of the insulating coaxial layer 42 and the interior surface of the heat transfer element 14. In addition, the spiraling invaginations 26 and the external surface 28 may be seen in FIG. 6. As noted above, in the preferred embodiment, the depth of the invaginations, $d_i$, is greater than the boundary layer thickness, $\delta$, which would have developed if a smooth heat transfer element were introduced. For example, in a heat transfer element with a 4 mm outer diameter, the depth of the invaginations, $d_i$, may be approximately equal to 1 mm if designed for use in the carotid artery. Although FIG. 6 shows five invaginations, the number of invaginations may vary. Thus, heat transfer elements with 1, 2, 3, 4, 5, 6, 7, 8 or more invaginations are specifically contemplated.

Figure 7:
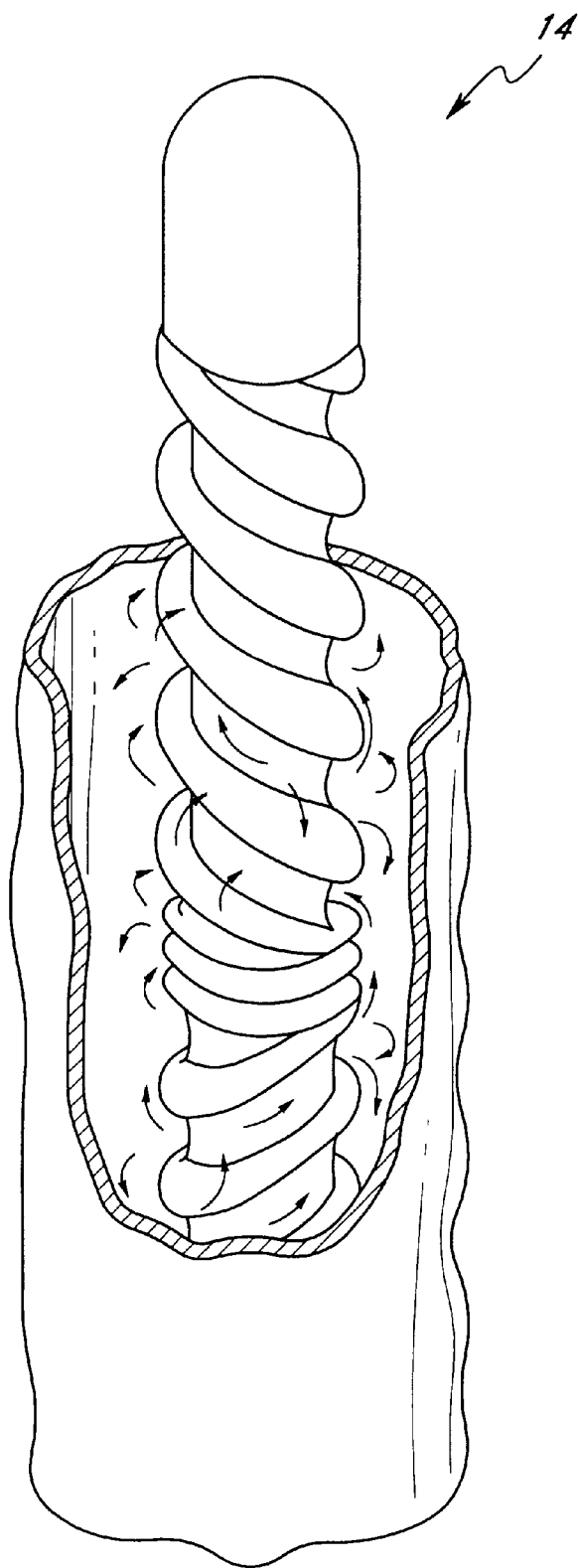
FIG. 7 is a cut-away perspective view of the heat transfer element of FIG. 4 in use within a blood vessel.

FIG. 7 is a cut-away perspective view of the heat transfer element 14 in use within a blood vessel. Beginning from the proximal end of the heat transfer element (not shown in FIG. 7), as the blood moves forward during the systolic pulse, the first invaginated segment induces a rotational inertia to the blood. As the blood reaches the second segment, the rotational direction of the inertia is reversed, causing turbulence within the blood. The sudden change in flow direction actively reorients and randomizes the velocity vectors, thus, ensuring turbulence throughout the bloodstream. During turbulent flow, the velocity vectors of the blood become more random and, in some cases, become perpendicular to the axis of the artery. In addition, as the velocity of the blood within the artery decreases and reverses direction during the cardiac cycle, additional turbulence is induced and turbulent motion is sustained throughout the duration of each pulse through the same mechanisms described above.

Thus, a large portion of the volume of warm blood in the vessel is actively brought in contact with the heat transfer element, where it can be cooled by direct contact, rather than being cooled largely by conduction through adjacent laminar layers of blood. As noted above, the depth of the invaginations is greater than the depth of the boundary layer which would develop if a smooth heat transfer element would be introduced into the blood stream. In this way, the free stream turbulence is induced. In introduced into the blood stream. In this way, the free stream turbulence is induced. In the preferred embodiment, in order to create the desired level of turbulence in the entire blood stream during the whole cardiac cycle, the heat transfer element creates a turbulence intensity greater than 0.05. The turbulence intensity may be greater than 0.055, 0.06, 0.07 or up to 0.10 or 0.20 or greater. If the heat transfer element according to the invention were placed in a pipe approximately the same size as an artery carrying a fluid having a similar velocity, density and viscosity of blood and having a constant (rather than pulsatile) flow, Reynolds numbers of greater than 1,900, 2,000, 2,100, 2,200 or even as much as 2,300, 2,400 or 2,600 or greater would be developed. Further, the design shown in FIGS. 4, 5, 6 and 7 provides a similar mixing action for the working fluid inside the heat transfer element.

The heat transfer element 14 has been designed to address all of the design criteria discussed above. First, the heat transfer element 14 is flexible and is made of highly conductive material. The flexibility is provided by a segmental distribution of bellows sections which provides an articulating mechanism. Bellows have a known convoluted design which provides flexibility. Second, the surface area has been increased through spiral invaginations or grooves. The invaginations also allow the heat transfer element to maintain a relatively atraumatic profile in comparison to the use of ribs or fins, thereby minimizing the possibility of damage to the vessel wall. Third, the heat transfer element 14 has been designed to promote turbulent kinetic energy both internally and externally. The modular or segmental design allows the direction of the invaginations to be reversed with each segment. The alternating invaginations create an alternating flow that results in mixing the blood in a manner analogous to the mixing action created by the rotor of a washing machine that switches directions back and forth. This mixing action is intended to promote the high level turbulent kinetic energy to enhance the heat transfer rate. The invaginated design also causes the beneficial mixing, or turbulent kinetic energy, of the working fluid flowing internally.

Figure 9:
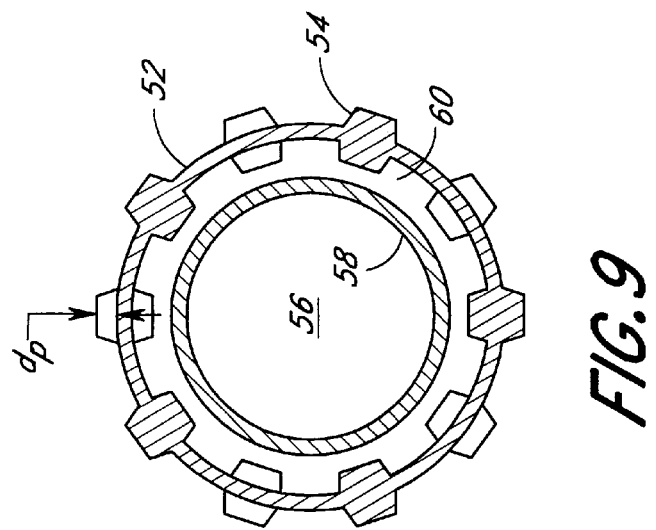
FIG. 9 is a transverse cross-sectional view of the heat transfer element of FIG. 8.
Figure 8:
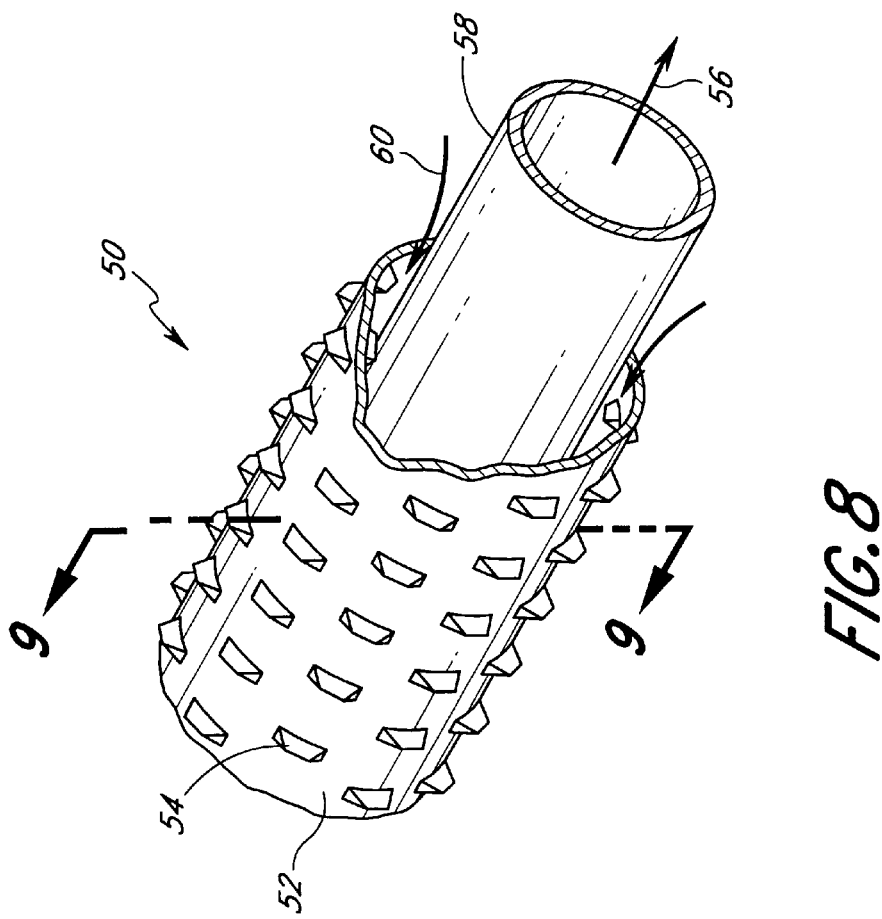
FIG. 8 is a cut-away perspective view of an alternative embodiment of a heat transfer element.

FIG. 8 is a cut-away perspective view of an alternative embodiment of a heat transfer element 50. An external surface 52 of the heat transfer element 50 is covered with a series of staggered protrusions 54. The staggered nature of the protrusions 54 is readily seen with reference to FIG. 9 which is a transverse cross-sectional view taken of the staggered protrusions 54 is greater than the thickness of the boundary layer which would develop if a smooth heat transfer element had been introduced into the blood stream. As the blood flows along the external surface 52, it collides with one of the staggered protrusions 54 and a turbulent flow is created. As the blood divides and swirls along side of the first staggered protrusion 54, it collides with another staggered protrusion 54 within its path preventing the re-lamination of the flow and creating yet more turbulence. In this way, the velocity vectors are randomized and free stream turbulence is created. As is the case with the preferred embodiment, this geometry also induces a turbulent effect on the internal coolant flow.

A working fluid is circulated up through an inner coaxial lumen 56 defined by an insulating coaxial layer 58 to a distal tip of the heat transfer element 50. The working fluid then traverses an outer coaxial lumen 50 in order to transfer heat to the exterior surface 52 of the heat transfer element 50. The inside structure of the heat transfer element 50 is similar to the exterior structure in order to induce turbulent flow of the working fluid.

Figure 10:
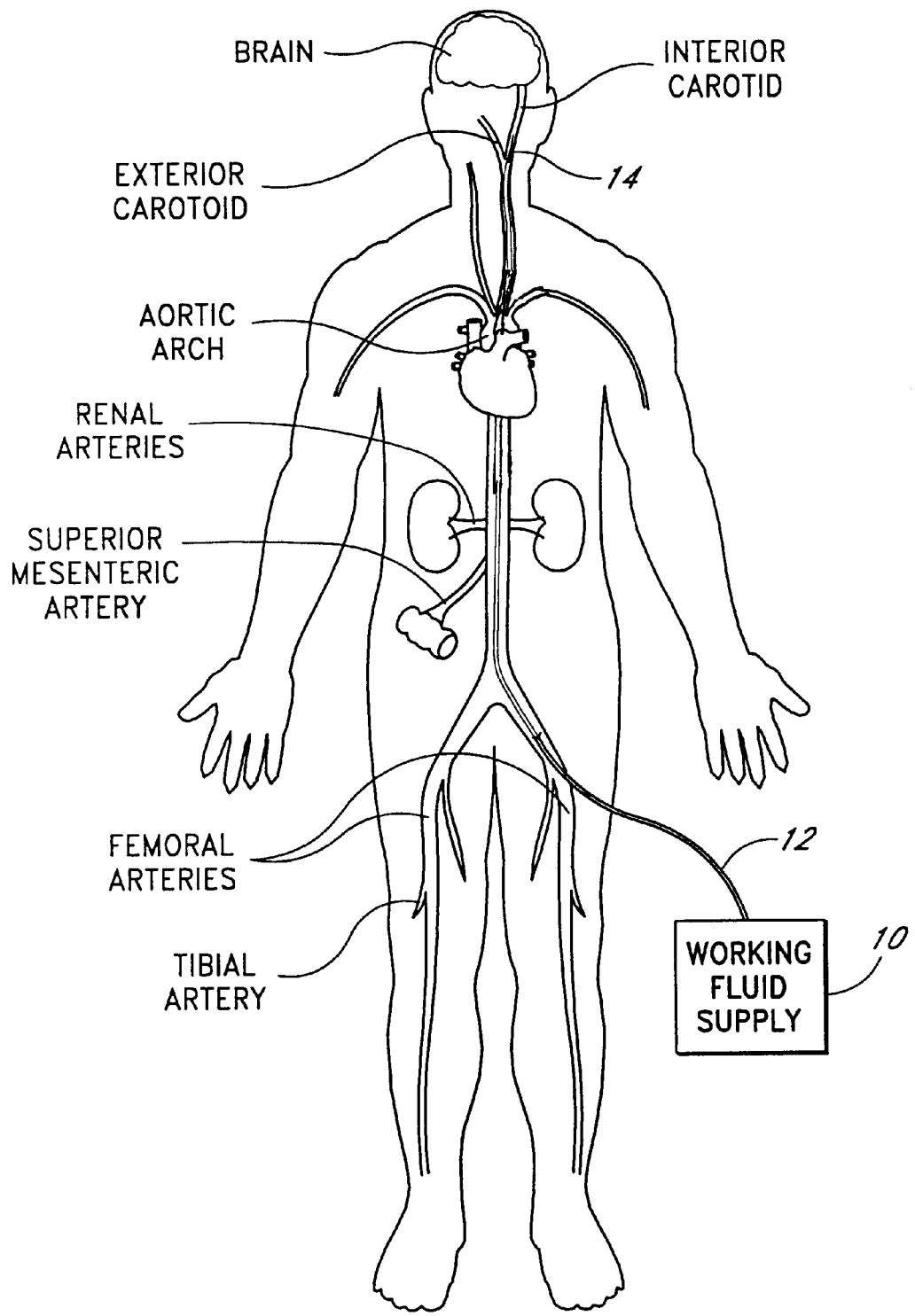
FIG. 10 is a schematic representation of the invention being used to cool the brain of a patient

FIG. 10 is a schematic representation of the invention being used to cool the brain of a patient. The selective organ hypothermia apparatus shown in FIG. 10 includes a working fluid supply 16, preferably supplying a chilled liquid such as water, alcohol or a halogenated hydrocarbon, a supply catheter 12 and the heat transfer element 14. The supply catheter 12 has a coaxial construction. An inner coaxial lumen within the supply catheter 12 receives coolant from the working fluid supply 16. The coolant travels the length of the supply catheter 12 to the heat transfer element 14 which serves as the cooling tip of the catheter. At the distal end of the heat transfer element 14, the coolant exits the insulated interior lumen and traverses the length of the heat transfer element 14 in order to decrease the temperature of the heat transfer element 14. The coolant then traverses an outer lumen of the supply catheter 12 so that it may be disposed of or recirculated. The supply catheter 12 is a flexible catheter having a diameter sufficiently small to allow its distal end to be inserted percutaneously into an accessible artery such as the femoral artery of a patient as shown in FIG. 10. The supply catheter 12 is sufficiently long to allow the heat transfer element 14 at the distal end of the supply catheter 12 to be passed through the vascular system of the patient and placed in the internal carotid artery or other small artery. The method of inserting the catheter into the patient and routing the heat transfer element 14 into a selected artery is well known in the art.

Although the working fluid supply 16 is shown as an exemplary cooling device, other devices and working fluids may be used. For example, in order to provide cooling, freon, perflourocarbon or saline may be used.

The heat transfer element of the present invention can absorb or provide over 75 Watts of heat to the blood stream and may absorb or provide as much a 100 Watts, 150 Watts, 170 Watts or more. For example, a heat transfer element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

The practice of the present invention is illustrated in the following non-limiting example.

EXEMPLE PROCEDURE

1. The patient is initially assessed, resuscitated, and stabilized.
2. The procedure is carried out in an angiography suite or surgical suite equipped with flouroscopy.
3. Because the catheter is placed into the common carotid artery, it is important to determine the presence of stenotic atheromatous lesions. A carotid duplex (doppler/ultrasound) scan can quickly and non-invasively make this determinations. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities>100 cm/sec in the internal indicate the presence of at least 70% stenosis. Stenosis of 70% or more may warrant the placement of a stent to open up the internal artery diameter.
4. The ultrasound can also be used to determine the vessel diameter and the blood flow and the catheter with the appropriately sized heat transfer element could be selected.
5. After assessment of the arteries, the patients inguinal region is sterilely prepped and infiltrated with lidocaine.
6. The femoral artery is cannulated and a guide wire may be inserted to the desired carotid artery. Placement of the guide wire is confirmed with flouroscopy.
7. An angiographic catheter can be fed over the wire and contrast media injected into the artery to further to assess the anatomy of the carotid.
8. Alternatively, the femoral artery is cannulated and a 10–12.5 french (f) introducer sheath is placed.
9. A guide catheter is placed into the desired common carotid artery. If a guiding catheter is placed, it can be used to deliver contrast media directly to further assess carotid anatomy.
10. A 10 f–12 f (3.3–4.0 mm) (approximate) cooling catheter is subsequently filled with saline and all air bubbles are removed.
11. The cooling catheter is placed into the carotid artery via the guiding catheter or over the guidewire. Placement is confirmed with flouroscopy.
12. Alternatively, the cooling catheter tip is shaped (angled or curved approximately 45 degrees), and the cooling catheter shaft has sufficient pushability and torqueability to be placed in the carotid without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. It subsequently enters the cooling catheter where it is delivered to the heat transfer element. The saline is warmed to approximately 5–7° C. as it travels along the inner lumen of the catheter shaft to the end of the heat transfer element.
16. The saline then flows back through the heat transfer element in contact with the inner metallic surface. The saline is further warmed in the heat transfer element to 12–15° C., and in the process, heat is absorbed from the blood cooling the blood to 30° C. to 32° C.
17. The chilled blood then goes on to chill the brain. It is estimated that 15–30 minutes will be required to cool the brain to 30 to 32° C.
18. The warmed saline travels back to down the outer lumen of the catheter shaft and back to the chilled water bath were it is cooled to 1° C.
19. The pressure drops along the length of the circuit are estimated to be 2–3 atmospheres.

20. The cooling can be adjusted by increasing or decreasing the flow rate of the saline. Monitoring of the temperature drop of the saline along the heat transfer element will allow the flow to be adjusted to maintain the desired cooling effect.

21. The catheter is left in place to provide cooling for 12 to 24 hours.

22. If desired, warm saline can be circulated to promote warming of the brain at the end of the therapeutic cooling period.

The design criteria described above for the heat transfer element, small diameter, high flexibility, use of highly conductive materials, and enhanced heat transfer rate through turbulent flow facilitate creation of a heat transfer element which successfully achieves selective organ cooling. The combination of these elements are not addressed in the prior art. In addition, these prior art references do not identify a mechanism for creating enhanced heat transfer rates through turbulent flow.

For example, U.S. Pat. No. 5,624,392 to Saab discloses a flexible coaxial catheter structure for transferring and removing heat from a remote body location, e.g., for cryosurgery or hyperthermic treatments. However, Saab discloses the use of an inflatable and collapsible balloon catheter formed from an elastomeric material. The elastomeric material is not highly conductive but instead the device relies on the thinning of the elastomeric walls in the inflated configuration in order to facilitate heat transfer. Even if such a design could be reduced in both diameter and length such that it could be placed within the feeding artery of an organ, it would not provide a sufficiently high heat transfer rate to lower the temperature of an organ to a beneficial level. The device disclosed in Saab does not create turbulent flow with a turbulence intensity of 0.05 or greater.

Likewise, U.S. Pat. No. 5,486,208 to Ginsberg describes a catheter which can be placed into a blood vessel in order to raise or lower the temperature of the entire body. The Ginsberg catheter is constructed from a flexible, non-conductive material. Several of the Ginsberg embodiments incorporate an inflatable and collapsible balloon structure at the distal end of the catheter. The balloon material has poor thermal conductivity and the device relies on increased surface area in the expanded configuration in order to increase the heat transfer properties of the catheter. Ginsberg discloses the use of longitudinal, radial or spiral fins to further increase the surface area of the catheter. Even with the enhanced surface area design, the catheter disclosed in Ginsberg would not provide the necessary heat transfer for organ-selective hypothermia, even if the diameter and length of the design could be reduced to fit into the feeding artery of an organ. As noted above, simple techniques commonly used to induce a transition from laminar to turbulence flow, such as "tripping" the boundary layer do not work in the arterial environment because the receptivity of the flow to this forcing is extremely low. Thus, placing small wires or fins on the surface of a device such as those disclosed in Ginsberg, does not create turbulent flow. The small fins or wires can create a local eddy of turbulence, however, they do not create free stream turbulence. In addition, the device disclosed in Ginsburg does not create turbulent flow with a turbulence intensity of 0.05 or greater.

In addition to small size, it is also important that a catheter be flexible in order to be placed within the small feeding artery of an organ. The Ginsberg and Saab devices are flexible. However, the flexibility of devices is achieved through the use of relatively non-conductive, inherently flexible materials. These materials do not facilitate good heat transfer properties in the devices. The Dato device is made from highly thermally conductive material but is not flexible and, therefore, not suited for insertion into the feeding artery of an organ. Further, the Dato device does not incorporate any surface features to promote turbulent kinetic energy, internally or externally. The device disclosed in Dato does not create turbulent flow with a turbulence intensity of 0.05 or greater.

Inducing selective organ hypothermia by intravascularly cooling the blood flow to that organ avoids many of the problems of the prior art. For example, because only a selected organ is cooled, complications associated with total body hypothermia are avoided. Because the blood is cooled intravascularly, or in situ, problems associated with external circulation of the blood are eliminated. Also, only a single puncture and arterial vessel cannulation is required which may be performed at an easily accessible artery such as the femoral, subclavian, or brachial arteries. By eliminating the use of a cold perfusate, problems associated with excessive fluid accumulation are avoided. In addition, rapid cooling to a precise temperature may be achieved. Further, treatment of a patient according to the invention is not cumbersome and the patient may easily receive continued care during the heat transfer process.

In addition, in some applications, it may be advantageous to attach a stent to the distal end of the heat transfer element. The stent may be used to open arteries partially obstructed by atheromatous disease prior to initiation of heat transfer. Further, the device may be used to deliver drugs such blood clot dissolving compounds (i.e. tissue plasminogen activator) or neuroprotective agents (i.e. selective neurotransmitter inhibitors). In addition to therapeutic uses, the device may be used to destroy tissue such as through cryosurgery.

In addition to the detailed description above, a myriad of alternate embodiments will be readily discernible to one skilled in the art. For example, the bellows sections may be made of flexible conductive or non-conductive material rather than metallic conductive material. In addition, a non-coaxial flow pattern may be used to transport the working fluid through the supply catheter. The working fluid may flow up the outer coaxial lumen and back down the inner coaxial lumen. In some cases, it may not be necessary to provide internal turbulence. In the embodiment above, turbulence was created using regular clockwise and counterclockwise invaginations on the exterior surface of the heat transfer element. However, other external surface configurations may create turbulent flow patterns.

The invention may be embodied in other specific forms without departing from its spirit or essential characteristics. The described embodiment is to be considered in all respects only as illustrative and not as restrictive and the scope of the invention is, therefore, indicated by the appended claims rather than the foregoing description. All changes which come within the meaning and range of equivalency of the claims are to be embraced within their scope.

What is claimed is:

1. A heat transfer device comprising:
   first and second elongated segments, each segment having a turbulence-inducing irregular exterior surface;
   a flexible articulating joint connecting the first and second elongated segments; and
   a tubular conduit disposed substantially coaxially within the first and second elongated, articulated segments, the conduit having an inner lumen for transporting a pressurized working fluid to a distal end of the elongated, articulated segments.

2. The device of claim 1, wherein the first and second elongated, articulated segments each have an irregular interior surface to induce turbulence within a pressurized working fluid.

3. The device of claim 1, wherein irregularities on the turbulence-inducing exterior surface are shaped and sized to induce a turbulence intensity within a free stream blood flow greater than 0.05.

4. The device of claim 1, wherein the turbulence-inducing exterior surfaces comprise invaginations configured to have a depth which is greater than a thickness of a boundary layer of blood which develops within an arterial flow.

5. The device of claim 1, wherein the first and second elongated, articulated segments comprise alternating clockwise and counter-clockwise invaginations.

6. The device of claim 1, wherein the first and second elongated, articulated segments are formed from highly conductive material.

7. The device of claim 1 further comprising:
a coaxial supply catheter having an inner catheter lumen coupled to the inner coaxial lumen within the first and second elongated, articulated segments; and
a working fluid supply configured to dispense the pressurized working fluid and having an output coupled to the inner catheter lumen.

8. The device of claim 7, wherein the working fluid supply is configured to produce the pressurized working fluid at about 0° C. and at a pressure below 5 atmospheres of pressure.

9. The device of claim 1, further comprising:
at least one additional elongated segment having a turbulence-inducing irregular exterior surface; and
at least one additional flexible articulating joint connecting the at least one additional elongated segment to one of the first and second elongated segments.

10. The device of claim 9, wherein the elongated, articulated segments comprise alternating clockwise and counterclockwise invaginations.

11. The device of claim 1, wherein the turbulence-inducing exterior surface is a clot-inhibiting surface.

12. The device of claim 1, further comprising a stent coupled to a distal end of the elongated, articulated segments.

13. The device of claim 1, wherein the flexible joint comprises an axially compressible bellows section.

14. A method of treating an organ, comprising:
inserting a flexible, conductive heat transfer element into a feeder artery from a distal location; and
circulating a working fluid through the flexible, conductive heat transfer element to modify the temperature of the blood in the feeder artery, thereby selectively modifying the temperature of the organ.

15. The method of claim 14, further comprising regulating the temperature and pressure of the working fluid to cause the flexible, conductive heat transfer element to absorb more than about 75 Watts of heat.

16. The method of claim 14, further comprising inducing turbulence within the free stream blood flow within the feeder artery.

17. The method of claim 16, further comprising inducing blood turbulence with a turbulence intensity greater than 0.05 within the feeder artery.

18. The method of claim 15, further comprising inducing blood turbulence throughout the period of the cardiac cycle within the feeder artery.

19. The method of claim 16, further comprising inducing blood turbulence throughout greater than 20% of the period of the cardiac cycle within the feeder artery.

20. The method of claim 14, further comprising inducing turbulent flow of the working fluid through the flexible, conductive heat transfer element.

21. The method of claim 18, wherein pressure of the working fluid is maintained below 5 atmospheres of pressure.

22. The method of claim 18, wherein the working fluid is aqueous.

23. A catheter for modifying the temperature of an organ, comprising:
a catheter shaft having first and second lumens therein;
a heat transfer tip adapted to transfer heat between blood surrounding the heat transfer tip and a working fluid circulated in through the first lumen and out through the second lumen; and
turbulence-inducing structures on the exterior of the heat transfer tip, the turbulence-inducing structures being shaped and sized to induce free stream turbulence in blood flowing within a blood vessel;
wherein the turbulence-inducing structures are shaped and sized to induce a turbulence intensity of at least about 0.05.

24. A catheter for modifying the temperature of an organ, comprising:
a catheter shaft having first and second lumens therein;
a heat transfer tip adapted to transfer heat between blood surrounding the heat transfer tip and a working fluid circulated in through the first lumen and out through the second lumen;
turbulence-inducing structures on the exterior of the heat transfer tip, the turbulence-inducing structures being shaped and sized to induce free stream turbulence in blood flowing within a blood vessel; and
turbulence-inducing structures on the interior of the heat transfer tip, the turbulence-inducing structures being shaped and sized to induce turbulence within the working fluid.

25. A catheter for modifying the temperature of an organ, comprising:
a catheter shaft having first and second lumens therein;
a heat transfer tip adapted to transfer heat between blood surrounding the heat transfer tip and a working fluid circulated in through the first lumen and out through the second lumen; and
turbulence-inducing structures on the exterior of the heat transfer tip, the turbulence-inducing structures being shaped and sized to induce free stream turbulence in blood flowing within a blood vessel;
wherein the turbulence-inducing structures comprise invaginations which have a depth sufficient to disrupt the free stream blood flow in the blood vessel.

26. A catheter for modifying the temperature of an organ, comprising:
a catheter shaft having first and second lumens therein;
a heat transfer tip adapted to transfer heat between blood surrounding the heat transfer tip and a working fluid circulated in through the first lumen and out through the second lumen; and
turbulence-inducing structures on the exterior of the heat transfer tip, the turbulence-inducing structures being shaped and sized to induce free stream turbulence in blood flowing within a blood vessel;
wherein the turbulence-inducing structures comprise staggered protrusions which have a height sufficient to disrupt the free stream flow of blood in the blood vessel.

27. A method of selectively inducing at least partial hypothermia in an organ of a patient, comprising:

providing a catheter with a flexible metallic heat transfer element disposed at a distal end thereof;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element; and cooling blood in the feeding artery by contact with the cooled heat transfer element.

28. A method of selectively inducing at least partial hypothermia in an organ of a patient, comprising:

providing a catheter with a flexible metallic heat transfer element disposed at a distal end thereof;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element;

cooling blood in the feeding artery by contact with the cooled heat transfer element; and cooling the organ by flow of the cooled blood through the feeding artery while maintaining the core body temperature at a substantially constant level.

29. A method of selectively inducing at least partial hypothermia in an organ of a patient, comprising:

providing a catheter with a flexible metallic heat transfer element disposed at a distal end thereof;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element;

cooling blood in the feeding artery by contact with the cooled heat transfer element; and cooling the organ by flow of the cooled blood through the feeding artery such that the organ temperature decreases substantially prior to reduction of the core body temperature.

30. A method of selectively inducing at least partial hypothermia in an organ of a patient, comprising:

providing a catheter with a flexible metallic heat transfer element disposed at a distal end thereof;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element, the working fluid being a liquid at temperatures in the range of about zero degrees Celsius to thirty-five degrees Celsius;

cooling blood in the feeding artery by contact with the cooled heat transfer element; and cooling the organ by flow of the cooled blood through the feeding artery while maintaining the core body temperature at a substantially constant level.

31. A method of selectively inducing at least partial hypothermia in an organ of a patient, comprising:

providing a catheter with a flexible metallic heat transfer element disposed at a distal end thereof;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element, the working fluid being a liquid at temperatures in the range of about zero degrees Celsius to thirty-five degrees Celsius;

cooling blood in the feeding artery by contact with the cooled heat transfer element; and cooling the organ by flow of the cooled blood through the feeding artery such that the organ temperature decreases substantially prior to reduction of the core body temperature.

32. A method of selectively inducing at least partial hypothermia in an organ of a patient, comprising:

providing a catheter with a flexible metallic heat transfer element disposed at a distal end thereof, the flexible metallic heat transfer element having at least one external flow-mixing feature disposed thereon;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element;

cooling blood in the feeding artery by contact with the cooled heat transfer element, the cooling enhanced by the external flow-mixing feature; and cooling the organ by flow of the cooled blood through the feeding artery while maintaining the core body temperature at a substantially constant level.

33. A method of selectively inducing at least partial hypothermia in an organ of a patient, comprising:

providing a catheter with a flexible metallic heat transfer element disposed at a distal end thereof, the flexible metallic heat transfer element having at least one external flow-mixing feature disposed thereon;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element;

cooling blood in the feeding artery by contact with the cooled heat transfer element, the cooling enhanced by the external flow-mixing feature; and cooling the organ by flow of the cooled blood through the feeding artery such that the organ temperature decreases substantially prior to reduction of the core body temperature.

34. A method of selectively inducing at least partial hypothermia in an organ of a patient, comprising:

providing a catheter with a flexible metallic heat transfer element disposed at a distal end thereof, the flexible metallic heat transfer element having at least one external flow-mixing feature disposed thereon;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element, the working fluid being a liquid at temperatures in the range of about zero degrees Celsius to thirty-five degrees Celsius; and cooling blood in the feeding artery by contact with the cooled heat transfer element, the cooling enhanced by the external flow-mixing feature.

35. A method of selectively inducing at least partial hypothermia in an organ of a patient, comprising:

providing a catheter with a flexible metallic heat transfer element disposed at a distal end thereof, the flexible metallic heat transfer element having at least one external flow-mixing feature disposed thereon;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element, the working fluid being a liquid at temperatures in the range of about zero degrees Celsius to thirty-five degrees Celsius;

cooling blood in the feeding artery by contact with the cooled heat transfer element, the cooling enhanced by the external flow-mixing feature; and cooling the organ by flow of the cooled blood through the feeding artery while maintaining the core body temperature at a substantially constant level.

36. A method of selectively inducing at least partial hypothermia in an organ of a patient, comprising:

providing a catheter with a flexible metallic heat transfer element disposed at a distal end thereof, the flexible metallic heat transfer element having at least one external flow-mixing feature disposed thereon;

inserting the catheter and heat transfer element into the vascular system of a patient to place at least a portion of the heat transfer element in a feeding artery of an organ;

circulating a working fluid through the catheter and through the heat transfer element to lower the temperature of the heat transfer element, the working fluid being a liquid at temperatures in the range of about zero degrees Celsius to thirty-five degrees Celsius;

cooling blood in the feeding artery by contact with the cooled heat transfer element, the cooling enhanced by the external flow-mixing feature; and cooling the organ by flow of the cooled blood through the feeding artery such that the organ temperature decreases substantially prior to reduction of the core body temperature.

37. A selective organ heat transfer device, comprising:

a flexible catheter capable of insertion to a selected feeding artery in the vascular system of a patient;

a plurality of heat transfer segments attached to a distal end of said catheter, at least one helical ridge and at least one helical groove formed on each of said plurality of heat transfer segments, said helical groove having a depth capable of inducing mixing in blood flow in the feeding artery, adjacent ones of said plurality of heat transfer segments disposed in close enough relation such that mixing arterial blood flow past one of said plurality of heat transfer segments does not relaminarize prior to passing an adjacent one of said plurality of heat transfer segments;

a bellows disposed between each of said plurality of heat transfer segments; and an inner tube disposed within each of said plurality of heat transfer segments and within each of said bellows, said inner tube being connected in fluid flow communication with an inner tube within said catheter.

38. A selective organ heat transfer device, comprising:

a flexible catheter capable of insertion to a selected vessel in the vascular system of a patient;

at least one heat transfer segment attached to a distal end of said catheter, said heat transfer segment having at least one mixing-inducing surface feature disposed thereon;

a bellows disposed adjacent and coaxial to said at least one heat transfer segment; and an inner tube disposed within said at least one heat transfer segment and within said bellows, said inner tube being connected in fluid flow communication with an inner tube within said catheter.

* * * * *

UNITED STATES PATENT AND TRADEMARK OFFICE
CERTIFICATE OF CORRECTION

PATENT NO. : 6,096,068
DATED : August 1, 2000
INVENTOR(S) : Dobak, III et al.

It is certified that error appears in the above-identified patent and that said Letters Patent is hereby corrected as shown below:

<u>Column 19,</u>
Line 59, "claim 15" to be changed to -- claim 19 --

Signed and Sealed this

Ninth Day of October, 2001

*Attest:*

NICHOLAS P. GODICI
*Attesting Officer*   Acting Director of the United States Patent and Trademark Office